United States Patent [19]

Monnier et al.

[11] Patent Number: 4,677,170
[45] Date of Patent: Jun. 30, 1987

[54] POLYEPOXIDES AND THE USE THEREOF

[75] Inventors: Charles E. Monnier, Villars-sur-Glâne; Sheik Abdul-Cader Zahir, Oberwil, both of Switzerland

[73] Assignee: Ciba-Geigy Corporaton, Ardsley, N.Y.

[21] Appl. No.: 870,608

[22] Filed: Jun. 4, 1986

[30] Foreign Application Priority Data

Jun. 6, 1985 [CH] Switzerland .................. 2399/85

[51] Int. Cl.⁴ .............................................. C08G 59/02
[52] U.S. Cl. ...................................... 525/539; 528/87; 528/101; 528/104
[58] Field of Search ...................... 528/87, 104, 101; 525/539

[56] References Cited

U.S. PATENT DOCUMENTS

| | | | |
|---|---|---|---|
| 2,965,607 | 12/1960 | Martin et al. | |
| 2,965,608 | 12/1960 | Martin et al. | |
| 4,282,345 | 8/1981 | Nelson | 528/104 X |
| 4,384,129 | 5/1983 | Zahir et al. | 528/101 X |
| 4,388,451 | 6/1983 | Culbertson et al. | 528/104 X |

*Primary Examiner*—Earl Nielsen
*Attorney, Agent, or Firm*—Luther A. R. Hall

[57] ABSTRACT

The invention relates to polyepoxides which are obtainable by reacting compounds of formula I

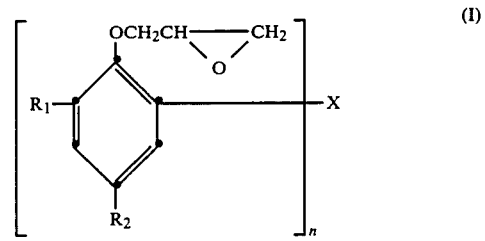

wherein n is 1 or 2, and X, if n is 1, is a group $R_3$, or, if n is 2, X is a group of the formula

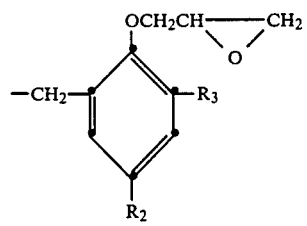

each of $R_1$ and $R_3$ independently of the other is $C_1$-$C_4$alkyl, $C_1$-$C_4$alkoxy, allyl, a halogen atom or $C_6$-$C_{10}$aryl and $R_2$ is allyl, 1-propenyl or 2-propenyl, with compounds containing phenolic OH groups, and subsequently epoxidizing the resultant adducts in the presence of a peracid. Said polyepoxides can be used, together with customary epoxy resin hardeners, for the preparation of cured products, in particular for coating electronic components, or as adhesives.

14 Claims, No Drawings

POLYEPOXIDES AND THE USE THEREOF

The present invention relates to novel polyepoxides, to curable mixtures containing such polyepoxides and to the use thereof, e.g. for the preparation of cured products, in particular for coating electronic components, or as adhesives.

British patent specification 828 364 describes, inter alia, higher molecular weight polyepoxides which are prepared by reacting o,o'-diallyl-substituted bisphenol A with diglycidyl ethers of bisphenol A, and subsequently epoxidising the resultant adducts with peracids.

The present invention relates to novel polyepoxides which are obtainable by reacting compounds of formula I

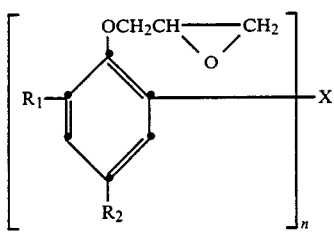

wherein n is 1 or 2, and X, if n is 1, is a group $R_3$, or, if n is 2, X is a group of the formula

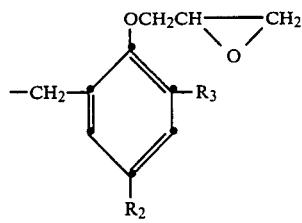

each of $R_1$ and $R_3$ independently of the other is $C_1$-$C_4$alkyl, $C_1$-$C_4$alkoxy, allyl, a halogen atom or $C_6$-$C_{10}$aryl and $R_2$ is allyl, 1-propenyl or 2-propenyl, with compounds containing phenolic OH groups, and subsequently epoxidising the resultant adducts in the presence of a peracid.

Alkyl and alkoxy substituents $R_1$ and $R_3$ may be straight chain or branched. Examples of such groups are: methyl, ethyl, n-propyl, isopropyl, n-butyl, sec-butyl, tert-butyl, methoxy, ethoxy, n-propoxy, isopropoxy, n-butoxy and sec-butoxy. Suitable aryl groups $R_1$ and/or $R_3$ are e.g. 1-naphthyl, 2-naphthyl and, in particular, phenyl. $R_1$ and/or $R_3$ as halogen atoms are e.g. bromine or fluorine atoms or, in particular, chlorine atoms.

It is preferred to use compounds of formula I wherein each of $R_1$ and $R_3$ independently of the other is $C_1$-$C_4$alkyl, $C_1$-$C_2$alkoxy, a halogen atom, in particular a chlorine atom, or phenyl and $R_2$ is allyl. In accordance with a further preference, compounds of formula I are used wherein $R_1$ and $R_3$ have the same meaning and $R_2$ is allyl. n is preferably 1. It is particularly preferred to use compounds of formula I wherein n is 1, each of $R_1$ and $R_3$ is methyl, tert-butyl, methoxy, chlorine or phenyl and $R_2$ is allyl. The most preferred compounds of formula I are those wherein n is 1, each of $R_1$ and $R_3$ is methyl and $R_2$ is allyl.

Suitable compounds containing phenolic OH groups for the preparation of the adducts are e.g. mono- and polyphenols which may be mono- or polynuclear, as well as reaction products of polyepoxides and an excess of polyphenols. Examples of mono- and polyphenols are: phenol, toluene, xylenes, 2-allylphenol, 2,6-diallylphenol, triallylphenol, resorcinol, hydroquinone, bis(4-hydroxyphenyl)methane (bisphenol F), 2,2-bis(4-hydroxyphenyl)propane (bisphenol A), 2,2-bis(4-hydroxy-3,5-dibromophenyl)propane (tetrabromobisphenol A), 2,2-bis(4-hydroxy-3-allylphenyl)propane, 2,2-bis(4-hydroxy-3,5-diallylphenyl)propane, bis(2-hydroxy-3-methyl-5-allylphenyl)methane, 2,2-bis(4-hydroxy-3-propenylphenyl)propane, 1,1,2,2-tetrakis(4-hydroxyphenyl)ethane, 4,4'-dihydroxybiphenyl, bis(4-hydroxyphenyl)sulfone, as well as novolaks of formaldehyde or acetaldehyde and phenol, chlorophenol, allylphenol or alkylphenols containing up to 9 carbon atoms in the alkyl moiety. Particularly preferred mono- and polyphenols are bisphenol A, bisphenol F, tetrabromobisphenol A, triallylphenol, 2,2-bis(4-hydroxy-3-allylphenyl)propane, 2,2-bis(4-hydroxy-3,5-diallylphenyl)propane, phenol/formaldehyde and cresol/formaldehyde novolaks.

For the reaction products of polyepoxides and an excess of polyphenols it is preferred to use mono- or polynuclear compounds of the above-mentioned type and epoxy resins containing on average more than one group of formula II

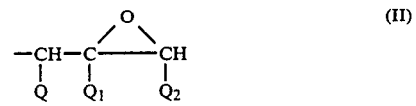

wherein each of Q and $Q_2$ is a hydrogen atom and $Q_1$ is a hydrogen atom or a methyl group or Q and $Q_2$ together are —$CH_2CH_2$— or —$CH_2$—$CH_2$—$CH_2$— and $Q_1$ is a hydrogen atom, which group is attached to a hetero atom, e.g. a sulfur atom and, preferably, to an oxygen or nitrogen atom.

Typical examples of such polyepoxides are polyglycidyl esters and poly($\beta$-methylglycidyl)esters which are derived from aliphatic, cycloaliphatic or aromatic polycarboxylic acids. Examples of suitable polycarboxylic acids are: succinic acid, glutaric acid, adipic acid, pimelic acid, suberic acid, azelaic acid, sebacic acid, dimerised or trimerised linoleic acid, tetrahydrophthalic acid, 4-methyltetrahydrophthalic acid, hexahydrophthalic acid, 4-methylhexahydrophthalic acid, phthalic acid, isophthalic acid and terephthalic acid.

Further examples are polyglycidyl esters and poly($\beta$-methylglycidyl)ethers which are obtained by reacting a compound containing at least two alcoholic and/or phenolic hydroxyl groups per molecule with epichlorohydrin or with allyl chloride, and then epoxidising the reaction product with a peracid. Examples of suitable polyols are ethylene glycol, diethylene glycol, poly(oxyethylene)glycols, propane-1,2-diol, poly(oxypropylene)glycols, propane-1,3-diol, butane-1,4-diol, poly(oxytetramethylene)glycols, pentane-1,5-diol, hexane-2,4,6-triol, glycerol, 1,1,1-trimethylolpropane, pentaerythritol and sorbitol; 1,3- and 1,4-cyclohexanediol, bis(4-hydroxycyclohexyl)methane, 2,2-bis(4-hydroxycyclohexyl)propane; and also aromatic polyols of the type indicated above.

Suitable poly(N-glycidyl)compounds are products obtained by dehydrochlorination of reaction products of epichlorohydrin and amines containing at least two active hydrogen atoms bonded to amino nitrogen atoms. Examples of suitable amines are: aniline, n-butylamine, bis(4-aminophenyl)methane, 1,3- and 1,4-xylylenediamine, 1,3- and 1,4-bis(aminomethyl)cyclohexane and bis(4-methylaminophenyl)methane. Further suitable compounds are: triglycidyl isocyanurate, N,N'-diglycidyl derivatives of cyclic alkylene ureas such as ethylene urea and 1,3-propylene urea, or hydantoins such as 5,5-dimethylhydantoin.

Examples of poly(S-glycidyl)compounds are the di-S-glycidyl derivatives of dithiols such as ethane-1,2-dithiol and bis(4-mercaptomethylphenyl)ether.

Examples of epoxy resins containing one or more groups of the formula II, wherein Q and $Q_2$ together are a —$CH_2CH_2$— or —$CH_2CH_2CH_2$— group are bis(2,3-epoxycyclopentyl)ether, 2,3-epoxycyclopentyl glycidyl ether, 1,2-bis(2,3-epoxycyclopentyloxy)ethane, 3,4-epoxy-6-methylcyclohexylmethyl-3',4'-epoxy-6'-methylcyclohexane carboxylate and 2-(3,4-epoxy)cyclohexyl-5,5-spiro(3',4'-epoxy)cyclohexane dioxane.

Preferred are reaction products of diglycidyl ethers of bisphenol A, bisphenol F or tetrabromobisphenol A or of polyglycidyl ethers of phenol/formaldehyde or cresol/formaldehyde novolaks and excess bisphenol A, bisphenol F and/or tetrabromobisphenol A.

Suitable peracids for the epoxidation of the adducts are in particular organic peracids, e.g. performic acid, peracetic acid, perbenzoic acid and monoperphthalic acid. The organic peracids can be employed as such or they can be formed in situ, for example from aliphatic or aromatic carboxylic acids, carboxylic acid anhydrides, carboxylates, acid chlorides or ketene and hydrogen peroxide. For the formation of the peracids in situ, it is preferred to use aliphatic or aromatic monocarboxylic dicarboxylic acids or the anhydrides thereof, e.g. formic acid, acetic acid, propionic acid, succinic anhydride, benzoic acid or phthalic acid, and hydrogen peroxide, optionally with the addition of acid catalysts such as sulfuric acid or alkali metal salts. The epoxidation of the adducts is preferably carried out in the presence of performic acid or peracetic acid, the acid being either preformed or produced in situ. If desired, inorganic peracids may also be used, e.g. permolybdic acid, pervanadic acid or pertungstic acid. The epoxidising agent (peracid) is conveniently used in an amount of at least 1 mole per allyl group present and is preferably used in excess, e.g. in a 20 to 200% molar excess. Thus if $R_1$ and/or $R_3$ are allyl, then these groups are also epoxidised.

The epoxidation of the adducts is advantageously carried out in the presence of inert organic solvents, optionally with the addition of buffers such as sodium acetate or sodium hydrogen phosphate. Examples of suitable solvents are unsubstituted or halogenated aliphatic or aromatic hydrocarbons such as chloroform, dichloromethane, benzene, toluene and chlorobenzene, ethers such as diethyl ether, diisopropyl ether, dioxane and tetrahydrofuran, as well as alkyl carboxylates such as ethyl acetate and n-butyl acetate. Preferred solvents are halogenated, in particular chlorinated, aliphatic hydrocarbons, with chloroform being particularly preferred. The epoxidation temperatures are generally in the range from $-10°$ to $+100°$ C., preferably from $+10°$ to $+60°$ C.

The compounds of formula I are known or they can be prepared by methods known per se by reacting the corresponding 2,6-disubstituted 4-allyl-, 4-(1-propenyl)- or 4-(2-propenyl)phenols of formula III

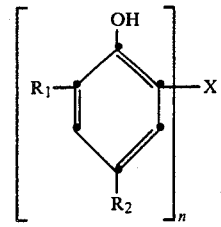

with epichlorohydrins, in particular epichlorohydrin, in the presence of catalysts, $R_1$, $R_2$, X and n in formula III are as defined above. Suitable phenols of formula III are e.g. 4-allyl-2,6-dimethylphenol, 4-allyl-2,6-dimethoxyphenol, 4-allyl-2,6-diisopropoxyphenol, 4-allyl-2,6-di-tert-butylphenol, 2,4,6-triallylphenol and bis(2-hydroxy-3-methyl-5-allylphenyl)methane.

The invention also relates to the novel adducts of compounds of formula I with compounds containing phenolic OH groups.

The adducts are prepared in a manner known per se in the melt or in an inert organic solvent and in the absence or presence of a catalyst. Examples of suitable inert solvents are unsubstituted or chlorinated aromatic hydrocarbons such as benzene, toluene and chlorobenzene; ketones such as acetone, methyl ethyl ketone and cyclohexanone; higher boiling alcohols such as butanols, isopropanol and 2-ethylhexanol. The reaction temperatures are generally in the range from 100° to 250° C., preferably from 120° to 180° C. The adduct formation is preferably effected in the melt. Acceptable catalysts are any compounds suitable for adduct formation, in particular alkali metal hydroxides, tertiary amines such as benzyldimethylamine, tris(dimethylaminomethyl)phenol, trimethylamine, triethylamine, octyldimethylamine, hexamethylenetetramine, as well as unsubstituted or substituted imidazoles such as imidazole, benzimidazole, 1-methylimidazole, 3-methylimidazole, 2-ethyl-4-methylimidazole, 2-phenylimidazole, 2-phenyl-4-methylimidazole and 1-(2,6-dichlorobenzoyl)-2-phenylimidazole. Tertiary amines, in particular benzyldimethylamine, and imidazoles, in particular 2-phenylimidazole, 3-methylimidazole and 2-ethyl-4-methylimidazole, are preferred catalysts.

The polyepoxides of this invention are pure substances which are free from chloride and alkali metal ions. Said polyepoxides are suitable for the preparation of cured products, e.g. for the coating of integrated circuits, for which purpose products of great purity are necessary. Accordingly, the invention also relates to curable mixtures containing (a) a polyepoxide of this invention and (b) a hardener for the component (a).

Mixtures of various polyepoxides of this invention and/or hardeners may also be employed. Suitable hardeners (b) are in general any epoxy resin hardeners such as cyanamide, dicyandiamide, polycarboxylic acids, polycarboxylic acid anhydrides, polyamines, polyaminoamides, adducts of amines with polyepoxides, and polyols.

Suitable polycarboxylic acids and their anhydrides are e.g. phthalic anhydride, tetrahydrophthalic anhydride, hexahydrophthalic anhydride, methyltetrahydrophthalic anhydride, endomethylenetetrahydrophthalic anhydride, hexachloroendomethylenetetrahydrophthalic anhydride, trimellitic anhydride, pyromellitic anhydride, maleic anhydride, succinic anhydride, nonenylsuccinic anhydride, dodecenylsuccinic anhydride, polysebacic polyanhydride and polyazelaic polyanhydride as well as the acids pertaining to said anhydrides.

Examples of polyamines which are suitable hardeners are aliphatic, cycloaliphatic, aromatic and heterocyclic polyamines such as ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)- and N-(2-cyanoethyl)diethylenetriamine, 2,2,4- and 2,4,4-trimethylhexane-1,6-diamine, m-xylylenediamine, N,N-dimethyl- and N,N-diethylpropane-1,3-diamine, bis(4-aminocyclohexyl)methane, 2,2-bis(4-aminocyclohexyl)propane, 2,2-bis(4-amino-3-methylcyclohexyl)propane, 3-aminomethyl-3,5,5-trimethylcyclohexylamine (isophoronediamine), m- and p-phenylenediamine, bis(4-aminophenyl)methane, bis(4-aminophenyl)sulfone, aniline/formaldehyde resins and N-(2-aminoethyl)piperazine. Suitable polyaminoamides are e.g. those which are prepared from aliphatic polyamines and dimerised or trimerised unsaturated fatty acids.

Suitable adducts of amines with polyepoxides are e.g. adducts of aliphatic or cycloaliphatic diamines such as 1,6-hexamethylenediamine, 2,2,4- and 2,4,4-trimethylhexane-1,6-diamine or isophoronediamine with known diglycidyl ethers.

Suitable polyol hardeners (b) are in particular mono- or polynuclear aromatic polyols, including novolaks, such as resorcinol, hydroquinone, 2,6-dihydroxytoluene, pyrogallol, 1,1,3-tris(hydroxyphenyl)propane, bis(4-hydroxyphenyl)methane, 2,2-bis(4-hydroxyphenyl)propane, bis(4-hydroxyphenyl)sulfone and 4,4'-dihydroxybiphenyl as well as novolaks of formaldehyde or acetaldehyde and phenol, chlorophenol or alkylphenols containing up to 9 carbon atoms in the alkyl moiety, in particular cresol and phenol novolaks.

Preferred hardeners are polycarboxylic acid anhydrides such as tetrahydrophthalic anhydride, hexahydrophthalic anhydride and methyltetrahydrophthalic anhydride, as well as aromatic polyamines, in particular bis(4-aminophenyl)methane, bis(4-aminophenyl)sulfone and m- or p-phenylenediamine.

The hardeners (b) are employed in the amounts conventionally used in the art of epoxy resins, and conveniently in such amounts that about 0.7 to 1.5 equivalents of functional groups of the hardener (b) are present per one epoxide equivalent.

The mixtures of this invention may also contain further customary additives, in particular (c) accelerators or curing catalysts and/or (d) further epoxy resins.

Compounds which are known per se may also be employed as accelerators (c), e.g.: complexes of amines, in particular tertiary amines such as monoethylamine, trimethylamine and octyldimethylamine, with boron trifluoride or boron trichloride, tertiary amines such as benzyldimethylamine, tris(dimethylaminomethyl)phenol, hexamethylenetetramine or 1,6-bis(dimethylamino)hexane; urea derivatives such as N-4-chlorophenyl-N',N'-dimethylurea (monuron), N-3-chloro-4-methylphenyl-N',N'-dimethylurea (chlortoluron), N-(2-hydroxyphenyl)-N',N'-dimethylurea and N-(2-hydroxy-4-nitrophenyl)-N',N'-dimethylurea, and unsubstituted or substituted imidazoles such as imidazole, benzimidazole, 1-methylimidazole, 2-ethyl-4-methylimidazole, 2-vinylimidazole, 2-phenylimidazole, 2-phenyl-4-methylimidazole, 1-(2,6-dichlorobenzoyl)-2-phenylimidazole and 1-(2,4,6-trimethylbenzoyl)-2-phenylimidazole.

Tertiary amines, in particular benzyldimethylamine, and imidazoles, in particular 2-phenylimidazole, 3-methylimidazole and 2-ethyl-4-methylimidazole, are preferred accelerators (c).

Suitable epoxy resins (d) are in particular those containing on average more than one group of formula II, which group is attached to a hetero atom, e.g. a sulfur atom and, preferably, to an oxygen or nitrogen atom, for example those resins described above.

As component (d) it is particularly preferred to use diglycidyl ethers or advanced diglycidyl ethers of dihydric phenols or cyclohexanols, in particular diglycidyl ethers or advanced diglycidyl ethers of 2,2-bis(4-hydroxyphenyl)propane, 2,2-bis(3,5-dibromo-4-hydroxyphenyl)propane, bis(4-hydroxyphenyl)methane, bis(4-hydroxycyclohexyl)methane or 2,2-bis(4-hydroxycyclohexyl)propoane; polyglycidyl ethers or novolaks, or tetraglycidylated 4,4'-diaminodiphenylmethane. Most preferred are diglycidyl ethers or advanced diglycidyl ethers of bisphenol A, tetrabromobisphenol A or bisphenol F, polyglycidyl ethers of phenol/formaldehyde or cresol/formaldehyde novolaks, or mixtures thereof.

The components (b) and (c) are employed in the customary effective amounts, i.e. in amounts sufficient for the curing of the mixtures of the invention. The ratio of the components (a), (b), (c) and, if present, (d) is dependent on the nature of the compounds employed, the required curing rate and the properties desired in the final product and can readily be determined by the person skilled in the art of epoxy resin curing. If the hardener (b) is an amine, then normally 0.75 to 1.25 equivalents of active hydrogen bonded to the amino nitrogen atoms are employed per epoxide equivalent. In the case of polycarboxylic acid or polycarboxylic acid anhydride hardeners, usually 0.4 to 1.1 equivalents of carboxyl or anhydride groups are employed per epoxide equivalent. If polyphenols are used as hardeners, then it is convenient to employ 0.75 to 1.25 phenolic hydroxyl groups per epoxide equivalent. Accelerators (c) are generally used in amounts of 0.1 to 5% by weight, based on the epoxy resins (a) and, if present, (d).

If desired, reactive diluents may be added to the curable mixtures in order to reduce the viscosity. Examples of such reactive diluents are styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary, aliphatic monocarboxylic acids. The mixtures of this invention may also contain, as further customary additives, plasticisers, extenders, fillers and reinforcing agents such as bituminous coal tar, bitumen, textile fibres, glass fibres, asbestos fibres, boron fibres, carbon fibres, mineral silicates, mica, quartz powder, aluminium oxide hydrate, betonites, kaolin, silica aerogel or metal powders, e.g. aluminium powder or iron powder, and also pigments and dyes such as carbon black, oxide pigments and titanium dioxide, flame retardants, thixotropic agents, flow control agents such as silicones, waxes and stearates (some of which are also employed as mould release agents), and adhesion promoters, antioxidants and light stabilisers.

The mixtures of this invention can be used e.g. as adhesives or for the preparation of cured products such as composite materials and laminates, in particular, however, for coating electronic components. The mixtures may be employed in a formulation adapted to the respective special field of application, in an unfilled or filled state, e.g. as coating compositions, varnishes, compression moulding compositions, dipping resins, casting resins, impregnating resins, laminating resins, matrix resins and adhesives.

The curing of the mixtures of this invention can be carried out in a manner known per se in one or two steps. The curing of the mixtures of this invention is generally effected by heating to temperatures in the range from 80° to 200° C., in particular from 100° to 180° C.

The cured products prepared with the polyepoxides of this invention are characterised by good mechanical, thermal and chemical properties.

The invention is illustrated in more detail by the following Examples.

A. Preparation of the starting material
(4-Allyl-2,6-dimethylphenyl glycidyl ether)

In a glass reaction vessel equipped with metering means, stirrer, thermometer and an azeotropic distillation head fitted with reflux condenser and vacuum attachment, 350 g (1 mole) of 4-allyl-2,6-dimethylphenol, 1796 g (19.42 moles) of epichlorohydrin and 16.20 g of tetramethylammonium chloride are mixed together, and the resultant mixture is heated to 60° C. and then stirred for 2 hours at 60° C. By applying a vacuum of 6700 Pa, the epichlorohydrin is brought to reflux at the reaction temperature (about 60° C.). In the course of 3.5 hours, 190 g of a 50% aqueous NaOH solution are added dropwise, the temperature of the reaction mixture being held at 60° C. During the reaction, the water formed is distilled off with the boiling epichlorohydrin. After the addition of the NaOH solution, the reaction mixture is stirred for about a further 2 hours. When the reaction is complete, the sodium chloride formed is filtered off, and the filtrate is neutralised with 1 liter of 10% Na$_2$SO$_4$ solution. The organic phase is separated and washed with two 600 ml portions of distilled water, separated from the aqueous phase and dried over sodium sulfate. Subsequently, the excess epichlorohydrin is distilled off at 60° C./2660 Pa by means of a rotary evaporator. Distillation of the residue at 110° C./1.3 Pa affords 358 g (75.5% of theory) of 4-allyl-2,6-dimethylphenyl glycidyl ether; epoxide content 4.54 equivalent/kg.

Elementary analysis: calculated; C 76.68%; H 8.73%; found: C 76.52%; H 8.43%.

$^1$H-NMR spectrum: 2.2 ppm (s) 6H (CH$_3$), ca. 2.75 ppm (m) 2H.

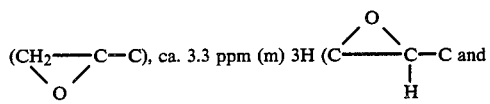

(CH$_2$—C—C), ca. 3.3 ppm (m) 3H (C—C—C and H

-continued

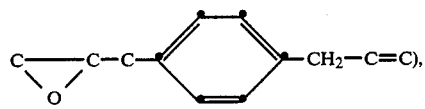

ca. 3.85 ppm (m) 2H

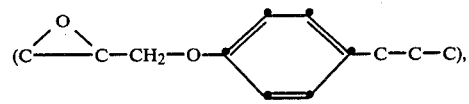

5.1 ppm (m) 2H (CH$_2$=C—C), 6.0 ppm (m) 1H (C=C—C), H

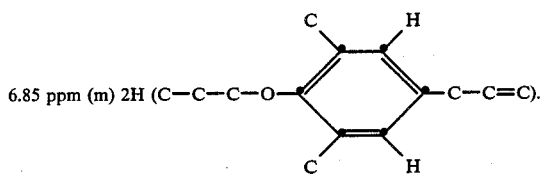

6.85 ppm (m) 2H (C—C—C—O—  —C—C=C).

Preparation of the adducts

EXAMPLE 1

30.84 g (0.1 phthalic OH equivalent) of 2,4,6-triallylphenol (compound B) and 43.86 g (0.1 epoxide equivalent) of 4-allyl-2,6-dimethylphenyl glycidyl ether (compound A) are mixed, and the mixture is dissolved at 80° C. 0.43 g of 2-phenylimidazole is dissolved in the resultant reddish brown mixture, and the mixture is heated to 180° C., whereupon the epoxide content of the adduct formed drops to about 0.15 equivalents/kg. The adduct has a melting viscosity of about 116 mPa at 100° C.

EXAMPLES 2 TO 5

In the manner described in Example 1, further adducts of compound A with the following polyols or novolaks are prepared:

EXAMPLE 2 o-cresol novolak containing 8.3 OH equivalents/kg

EXAMPLE 3

2,2-bis(4-hydroxy-3,5-diallylphenyl)propane

EXAMPLE 4

2,2-bis(4-hydroxy-3-allylphenyl)propane

EXAMPLE 5 bis(2-hydroxy-3-methyl-5-allylphenyl)methane.

The reaction conditions and the melting viscosities of the resultant products are shown in the following Table I.

TABLE I

| Ex. | Compound A (g) | Compound B (g) | 2-Phenylimidazole (g) | Reaction time/ reaction temperature h/0° C. | Melting viscosity mPa s/100° C. |
|---|---|---|---|---|---|
| 2 | 87.7 | 61.6 g of o-cresol novolak | 0.015 | 4/175 | 206 |
| 3 | 21.83 | 21.05 g of 2,2-bis(4-hydroxy-3,5-diallylphenyl)propane | 0.22 | 3/166 | 210 |
| 4 | 21.83 | 21.42 g of 2,2-bis(4-hydroxy- | 0.22 | 4/170 | 10 |

TABLE I-continued

| Ex. | Compound A (g) | Compound B (g) | 2-Phenylimidazole (g) | Reaction time/ reaction temperature h/0° C. | Melting viscosity mPa s/100° C. |
|---|---|---|---|---|---|
| 5 | 43.8 | 3-allylphenyl)propane 24.1 g of bis(2-hydroxy-3-methyl-5-allylphenyl)methane | 0.0024 | 6/180 | 10 |

Epoxidation of the adducts

EXAMPLE 6

A 350 ml sulfurating flask equipped with stirrer, cooler, drip funnel and thermometer is charged with 37.5 g (0.087 mole) of the adduct (prepared according to Example 1) of 4-allyl-2,6-dimethylphenyl glycidyl ether with 2,4,6-triallylphenol in 50 ml of chloroform and 0.1 g of sodium acetate. Over about 2 hours, 66.12 g (0.348 mole) of 40% peracetic acid are added dropwise at 30°-35° C. The reaction mixture is stirred for a further 6 hours, then transferred to a separating funnel, washed first with 3% NaOH and then with water, made peroxide-free with Na₂SO₃, dried over sodium sulfate and concentrated, affording 27.63 g (63.96% of theory) of a highly viscous resin with an epoxide content of 4.539 equivalents/kg (about 56.3% of theory). The following molecular weights are determined by gel chromatography:
$M_n$ (number average)=570
$M_w$ (weight average)=814.

EXAMPLE 7

A 200 ml sulfurating flask equipped with stirrer, cooler, drip funnel and thermometer is charged with 62.0 g (182 mmol) of the adduct (prepared according to Example 2) of 4-allyl-2,6-dimethylphenyl glycidyl ether with o-cresol novolak in 50 ml of chloroform. Over 90 minutes, 41.80 g (220 mmol) of 40% peracetic acid are added dropwise at 30°-35° C. When the dropwise addition is complete, the reaction mixture is stirred for a further 16 hours. For working up, the resultant product is washed with 3% NaOH and then with aqueous sodium chloride solution, made peroxide-free with Na₂SO₃, dried over sodium sulfate and concentrated, affording 35.16 g of a solid epoxy resin with the epoxide content of 2.372 equivalents/kg.

EXAMPLE 8

A 200 ml sulfurating flask equipped with stirrer, cooler, thermometer and drip funnel is charged with 30.0 g (0.036 mole) of the adduct (prepared according to Example 3) of 4-allyl-2,6-dimethylphenyl glycidyl ether with 2,2-bis(4-hydroxy-3,5-diallylphenyl)propane in 50 ml of chloroform and 1.0 g of sodium acetate. Over 90 minutes, 41.80 g (0.22 mole) of 40% peracetic acid are added dropwise at 30°-50° C. The reaction mixture is stirred for a further 6 hours and then transferred to a separating funnel. The resultant reaction product is washed with 3% NaOH solution and then with NaCl solution, made peroxide-free with sodium sulfite, dried over sodium sulfate and concentrated. The solvent is removed, affording 27.65 g (92.2% of theory) of a highly viscous epoxy resin with an epoxide content of 5.097 equivalents/kg (70% of theory).

EXAMPLE 9

A 350 ml sulfurating flask equipped with stirrer, thermometer, cooler and drip funnel is charged with 50 g of the adduct (prepared according to Example 4) of 4-allyl, 2,6-dimethylphenyl glycidyl ether with 2,2-bis(4-hydroxy-3-allylphenyl)propane in 50 ml of chloroform. Over about 120 minutes, 54.96 g (0.29 mole) of 40% peracetic acid are added dropwise at 30°-35° C. The reaction mixture is stirred for a further 4 hours, transferred to a separating funnel, washed with 3% NaOH and then with water, made peroxide-free with sodium sulfite, dried over sodium sulfate and concentrated, affording 43.12 g of a brownish solid epoxy resin with an epoxide content of 3.46 equivalents/kg.

EXAMPLE 10

A 200 ml sulfurating flask equipped with drip funnel, stirrer, cooler and thermometer is charged with 40.0 g (0.054 mole) of the adduct (prepared according to Example 5) of 4-allyl-2,6-dimethylphenyl glycidyl ether with bis(2-hydroxy-3-methyl-5-allylphenyl)methane in 50 ml of chloroform and 1.0 g of sodium acetate. Over about 2 hours, 66.12 g (0.348 mole) of 40% peracetic acid are added dropwise at 30°-35° C. After stirring for a further 5 to 6 hours, the reaction product is worked up in accordance with the procedure indicated in Example 6, affording 43.2 (98.64% of theory) of a highly viscous epoxy resin with an epoxide content of 3.65 equivalents/kg (73.94% of theory).

Application Examples I to V

Each of the epoxy resins obtained according to Examples 7, 8 and 10 is mixed with a hardener and a curing accelerator (2-ethyl-4-methylimidazole) and processed to a cured moulded article. The nature and amount of the components employed, the curing conditions and the properties of the cured moulded articles are shown in the following Table II.

TABLE II

| Application Example | Epoxy resin acc. to Ex. | g | Hardener[1] (g) | 2-Ethyl-4 methylimidazole (g) | Curing conditions time/temp. | Properties of the cured moulded article $T_g$[2] |
|---|---|---|---|---|---|---|
| II | 7 | 41.82 | 18.07 | 0.04 | 4 h/180° C. | 134° C. |
| III | 8 | 26.46 | 15.66 | 0.13 | 2 h/120° C. 2 h/150° C. 2 h/180° C. | 142° C. |
| V | 10 | 8.44 | 2.41 | 0.008 | 4 h/180° C. | 116° C. |

[1] hardener = o-cresol novolak containing 8.3 equivalents of phenolic OH groups/kg
[2] determined by differential scanning calorimetry (DSC) using a Mettler TA 3000 analyser

What is claimed is:
1. A polyepoxide which is obtainable by reacting a compound of formula I

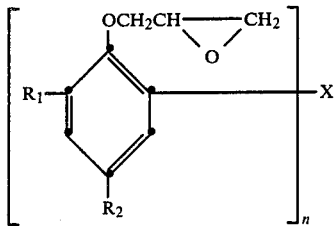

(I)

wherein n is 1 or 2, and X, if n is 1, is a group R₃, or, if n is 2, X is a group of the formula

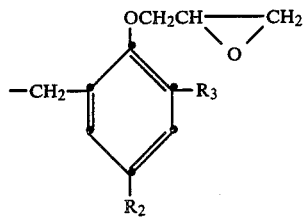

each of $R_1$ and $R_3$ independently of the other is $C_1$–$C_4$alkyl, $C_1$–$C_4$alkoxy, allyl, a halogen atom or $C_6$–$C_{10}$aryl and $R_2$ is allyl, 1-propenyl or 2-propenyl, with a compound containing phenolic OH groups, and subsequently epoxidising the resultant adduct in the presence of a peracid.

2. A polyepoxide according to claim 1, wherein each of $R_1$ and $R_3$ independently of the other is $C_1$–$C_4$alkyl, $C_1$–$C_2$alkoxy, a halogen atom, in particular a chlorine atom, or phenyl and $R_2$ is allyl.

3. A polyepoxide according to claim 1, wherein $R_1$ and $R_3$ have the same meaning and $R_2$ is allyl.

4. A polyepoxide according to claim 1, wherein n is 1.

5. A polyepoxide according to claim 1, wherein n is 1, each of $R_1$ and $R_3$ is methyl, tert-butyl, methoxy, chlorine or phenyl and $R_2$ is allyl.

6. A polyepoxide according to claim 1, wherein n is 1, each of $R_1$ and $R_3$ is methyl and $R_2$ is allyl.

7. A polyepoxide according to claim 1, which is obtainable by using a mono- or polynuclear mono- or polyphenol as the compound containing phenolic OH groups.

8. A polyepoxide according to claim 7, which is obtainable by using bisphenol A, bisphenol F, tetrabromobisphenol A, triallylphenol, 2,2-bis(4-hydroxy-3-allylphenyl)propane, 2,2-bis(4-hydroxy-3,5-diallylphenyl)propane, a phenol/formaldehyde or cresol/formaldehyde novolak as the mono- or polyphenol.

9. A polyepoxide according to claim 1, which is obtainable by using a reaction product of a polyepoxide and an excess of one or more polyphenols as the compound containing phenolic OH groups.

10. A polyepoxide according to claim 9, which is obtainable by using a reaction product of a diglycidyl ether of bisphenol A, bisphenol F or tetrabromobisphenol A or of a polyglycidyl ether of a phenol/formaldehyde or cresol/formaldehyde novolak and excess bisphenol A, bisphenol F and/or tetrabromobisphenol A.

11. A polyepoxide according to claim 1, which is obtainable by carrying out the epoxidation in the presence of performic acid or peracetic acid.

12. An adduct of a compound of formula I

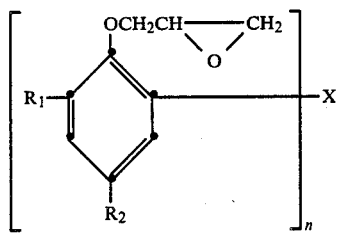

(I)

wherein n is 1 or 2, and X, if n is 1, is a group R₃, or, if n is 2, X is a group of the formula

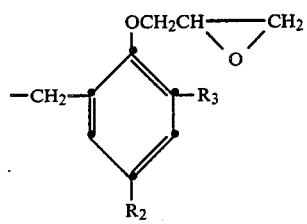

each of $R_1$ and $R_3$ independently of the other is $C_1$–$C_4$alkyl, $C_1$–$C_4$alkoxy, allyl, a halogen atom or $C_6$–$C_{10}$aryl and $R_2$ is allyl, 1-propenyl or 2-propenyl, with a compound containing phenolic OH groups.

13. A curable mixture containing
(a) a polyepoxide of this invention according to claim 1 and
(b) a hardener for the component (a).

14. A curable mixture according to claim 13, which additionally contains (c) a curing accelerator.

* * * * *